(12) United States Patent
Miller et al.

(10) Patent No.: US 6,806,463 B2
(45) Date of Patent: Oct. 19, 2004

(54) MICROMACHINED FIELD ASYMMETRIC ION MOBILITY FILTER AND DETECTION SYSTEM

(75) Inventors: Raanan A. Miller, Brookline, MA (US); Erkinjon G. Nazarov, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 10/321,822

(22) Filed: Dec. 16, 2002

(65) Prior Publication Data

US 2003/0132380 A1 Jul. 17, 2003

Related U.S. Application Data

(63) Continuation-in-part of application No. 09/358,312, filed on Jul. 21, 1999, now Pat. No. 6,495,823.

(51) Int. Cl.[7] .............................................. H01J 49/40
(52) U.S. Cl. ...................... 250/286; 250/287; 250/288; 250/281; 250/282; 250/285
(58) Field of Search ................................ 250/286, 288, 250/287, 281, 282, 285

(56) References Cited

U.S. PATENT DOCUMENTS

| | | | |
|---|---|---|---|
| 2,615,135 A | 10/1952 | Glenn, Jr. | |
| 2,818,507 A | 12/1957 | Britten | |

(List continued on next page.)

FOREIGN PATENT DOCUMENTS

| | | |
|---|---|---|
| BR | 966583 | 10/1982 |
| DE | 1337934 A2 | 9/1987 |
| DE | 1627984 A2 | 2/1991 |
| DE | 1405489 A1 | 6/1998 |
| DE | 1412447 A1 | 6/1998 |
| DE | 1485808 A1 | 6/1998 |
| WO | WO 96/19822 | 6/1996 |
| WO | WO 97/38302 | 10/1997 |
| WO | WO 99/21212 | 4/1999 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 08197 A1 | 2/2001 |
| WO | WO 22049 A2 | 3/2001 |
| WO | WO 35441 A1 | 5/2001 |
| WO | WO 01/69220 A2 | 9/2001 |
| WO | WO 01/69647 A2 | 9/2001 |
| WO | WO 02/071053 A | 9/2002 |

OTHER PUBLICATIONS

Guevremont, R. et al., "Atmospheric Pressure Ion Focusing in A High–Field Asymmetric Waveform Ion Mobility Spectrometer," *Review of Scientific Instruments*, 70(2): 1370–1383 (1999).

E. V. Krylov, "A Method of Reducing Diffusion Losses in A Drift Spectrometer," *Technical Physics*, 4d(1): 113–116 (1999).

(List continued on next page.)

Primary Examiner—John R. Lee
Assistant Examiner—Zia R. Hashmi
(74) Attorney, Agent, or Firm—Ropes & Gray LLP

(57) ABSTRACT

A micromechanical field asymmetric ion mobility filter for a detection system includes a pair of spaced substrates defining between them a flow path between a sample inlet and an outlet; an ion filter disposed in the path and including a pair of spaced filter electrodes, one electrode associated with each substrate; and an electrical controller for applying a bias voltage and an asymmetric periodic voltage across the ion filter electrodes for controlling the paths of ions through the filter.

27 Claims, 13 Drawing Sheets

U.S. PATENT DOCUMENTS

| | | |
|---|---|---|
| 2,919,348 A | 12/1959 | Bierman |
| 3,511,986 A | 5/1970 | Llewellyn |
| 3,619,605 A | 11/1971 | Cook et al. |
| 3,621,240 A | 11/1971 | Cohen et al. |
| 3,648,046 A | 3/1972 | Denison et al. |
| 3,931,589 A | 1/1976 | Aisenberg et al. |
| 4,019,989 A | 4/1977 | Hazewindus et al. |
| 4,025,818 A | 5/1977 | Giguere et al. |
| 4,136,280 A | 1/1979 | Hunt et al. |
| 4,163,151 A | 7/1979 | Bayless et al. |
| 4,167,668 A | 9/1979 | Mouriér |
| 4,201,921 A | 5/1980 | McCorkle |
| 4,315,153 A | 2/1982 | Vahrenkamp |
| 4,517,462 A | 5/1985 | Boyer et al. |
| 4,761,545 A | 8/1988 | Marshall et al. |
| 4,885,500 A | 12/1989 | Hansen et al. |
| 4,931,640 A | 6/1990 | Marshall et al. |
| 5,019,706 A | 5/1991 | Allemann et al. |
| 5,047,723 A | 9/1991 | Puumalainen |
| 5,144,127 A | 9/1992 | Williams et al. |
| 5,218,203 A | 6/1993 | Eisele et al. |
| 5,298,745 A | 3/1994 | Kernan et al. |
| 5,373,157 A | 12/1994 | Hiroki et al. |
| 5,420,424 A | 5/1995 | Carnahan et al. |
| 5,455,417 A | 10/1995 | Sacristan |
| 5,492,867 A | 2/1996 | Kotvas et al. |
| 5,536,939 A | 7/1996 | Freidhoff et al. |
| 5,541,408 A | 7/1996 | Sittler |
| 5,644,131 A | 7/1997 | Hansen |
| 5,654,544 A | 8/1997 | Dresch |
| 5,723,861 A | 3/1998 | Carnahan et al. |
| 5,736,739 A | 4/1998 | Uber et al. |
| 5,763,876 A | 6/1998 | Pertinarides et al. |
| 5,789,745 A | 8/1998 | Martin et al. |
| 5,801,379 A | 9/1998 | Kouznetsov |
| 5,811,059 A | 9/1998 | Genovese et al. |
| 5,834,771 A | 11/1998 | Yoon et al. |
| 5,838,003 A | 11/1998 | Bertsch et al. |
| 5,852,302 A | 12/1998 | Hiraishi et al. |
| 5,869,344 A | 2/1999 | Linforth et al. |
| 5,965,882 A | 10/1999 | Megerle et al. |
| 6,049,052 A | 4/2000 | Chutjian et al. |
| 6,051,832 A | 4/2000 | Bradshaw |
| 6,066,848 A | 5/2000 | Kassel et al. |
| 6,107,628 A | 8/2000 | Smith et al. |
| 6,124,592 A | 9/2000 | Spangler |
| 6,157,029 A | 12/2000 | Chutjian et al. |
| 6,157,031 A | 12/2000 | Prestage |
| 6,188,067 B1 | 2/2001 | Chutjian et al. |
| 6,200,539 B1 | 3/2001 | Sherman et al. |
| 6,262,416 B1 | 7/2001 | Chutjian et al. |
| 6,281,494 B1 | 8/2001 | Chutjian et al. |
| 6,323,482 B1 | 11/2001 | Clemmer et al. |
| 6,495,823 B1 | 12/2002 | Miller et al. |
| 6,504,149 B2 | 1/2003 | Guevremont et al. |
| 6,509,562 B1 | 1/2003 | Yang et al. |
| 6,618,712 B1 | 9/2003 | Parker et al. |
| 2001/0030285 A1 | 10/2001 | Miller et al. |
| 2002/0070338 A1 | 6/2002 | Loboda |
| 2002/0134932 A1 | 9/2002 | Guevremont |
| 2003/0089847 A1 | 5/2003 | Guevremont et al. |

OTHER PUBLICATIONS

"Advanced Cross–Enterprise Technology Development for NASA Missions," Revised NASA Research Announcement NRA99–OSS–05 pp. 1–C19 (1999).

Buryakov, et al., "Drift Spectrometer for the Control of Amine Traces in the Atmosphere," *J. Anal. Chem.*48(1):112–121 (1993).

Handy, et al., "Determination of Nanomolar Levels of Perchlorate in Water by ESI–FAIMS–MS," *J. Anal. At. Spectrometry*15:907–911 (2000).

Buryakov, et al., "Separation of Ions According to Mobility in A Strong AC Electric Field," *Letters to Journal of Technical Physics*, 17:11–12 (1991).

Guevremont, Roger and Purves, Randy W., "High Field Asymmetric Waveform Ion Mobility Spectrometry–Mass Spectrometry: An Investigation of Leucine Enkephalin Ions Produced by Electrospray Ionization," *J. Am. Soc. Mass. Spectrom.*10:492–501 (1999).

Verenchikov, A.N. et al., "Analysis of Ionic Composition of Solutions Using, an Ions Gas Analyzer. Chemical Analysis of the Environment," *J. Am. Soc. Mass. Spectrom.*10:492–501 (1999).

Reigner, D.E., et al., "Qualitative Evaluation of Field Ion Spectrometry for Chemical Warfare Agent Detection," Proceedings of The ASMS Conference on Mass Spectrometry and Allied Topics, pp. 473A–473B, (Jun., 1997).

Carnahan, B., et al., "Field Ion Spectrometry –A New Analytical Technology for Trace Gas Analysis," *ISA*, 51(1):87–96, (1996).

Carnahan, B., et al., "Field Ion Spectrometry –A New Technology for Cocaine and Heroin Detection," *SPIE*, 2937:106–119, (1997).

Buryakov, I.A. et al., "A New Method of Separation of Multi–Atomic Ions by Mobility at Atmospheric Pressure Using a High–Frequency Amplitude–Asymmetric Strong Electric Field," *International Journal of Mass Spectrometry and Ion Processes*, 128:143–148, (1993).

Miller, R.A., et al., "A Novel Micromachined High–Field Asymmetric Waveform–Ion Mobility Spectrometer," *Sensors and Actuators B*, B67(3):300–306, (2000).

Barnett, D.A., et al., "Isotope Separation Using High–Field Asymmetric Waveform Ion Mobility Spectrometry," *Nuclear Instruments & Methods in Physics Research*, 450(1):179–185, (2000).

Guevremont, R., et al., "Calculation of Ion Mobilities From Electrospray Ionization High–Field Asymmetric Waveform Ion Mobility Spectrometry Mass Spectrometry," *Journal of Chemical Physics*, 114(23):10270–10277, (2001).

Pilzecker, P., et al., "On–Site Investigations of Fas Insulated Substations Using Ion Mobility Spectrometry for Remote Sensing of $SF_6$Decompositions," *IEEE*, pp. 400–403, (2000).

Krylov, E.V., "Pulses of Special Shapes Formed on a Capacitive Load," *Instruments and Experimental Techniques*, 40(5):628, (1197).

Burykov, I.A., et al., Device and Method For Gas Electrophoresis, Chemical Analysis of Environment, edit. Prof. V. V. Malakhov, Novosibirsk: Nauka, (1991) pp. 113–127.

Raizer, Y. P., et al., Radio–Frequency Capacitive Discharges, *CRC Press*, pp. 1–3, (1995).

"A Micromachined Field Driven Radio Frequency–Ion Mobility Spectrometer for Trace Level Chemical Detection," A Draper Laboratory Proposal Against the "Advanced Cross–Enterprise Technology Development for NASA Missions," Solicitation, NASA NRA 99–OSS–05.

Javahery, G., et al., "A Segmented Radiofrequency–Only Quadrupole Collision Cell for Measurements of Ion Collision Cross Section on a Triple Quadrupole Mass Spectrometer," *J. Am. Soc. Mass. Spectrom.*8:697–702 (1997).

MICROMACHINED FIELD ASYMMETRIC ION MOBILITY FILTER AND DETECTION SYSTEM

RELATED APPLICATIONS

This application is a continuation-in-part of U.S. application Ser. No. 09/358,312 filed Jul. 21, 1999 is now U.S. Pat. No. 6,495,823. The entire teachings of the above application are incorporated herein by reference.

BACKGROUND OF THE INVENTION

This invention relates to a Field Asymmetric Ion Mobility (FAIM) filter, and more particularly, to a micromachined FAIM filter and spectrometer.

The ability to detect and identify explosives, drugs, chemical and biological agents as well as air quality has become increasingly more critical given increasing terrorist and military activities and environmental concerns. Previous detection of such agents was accomplished with conventional mass spectrometers, time of flight ion mobility spectrometers and conventionally machined FAIM spectrometers.

Mass spectrometers are very sensitive, highly selective and provide a fast response time. Mass spectrometers, however, are large and require significant amounts of power to operate. They also require a powerful vacuum pump to maintain a high vacuum in order to isolate the ions from neutral molecules and permit detection of the selected ions, and are also very expensive.

Another spectrometric technique which is less complex is time of flight ion mobility spectrometry which is the method currently implemented in most portable chemical weapons and explosives detectors. The detection is based not solely on mass, but on charge and cross-section of the molecule as well. However, because of these different characteristics, molecular species identification is not as conclusive and accurate as the mass spectrometer. Time of flight ion mobility spectrometers typically have unacceptable resolution and sensitivity limitations when attempting to reduce their size, that is a drift tube length less than 2 inches. In time of flight ion mobility, the resolution is proportional to the length of the drift tube. The longer the tube the better the resolution, provided the drift tube is also wide enough to prevent all ions from being lost to the side walls due to diffusion. Thus, fundamentally, miniaturization of time of flight ion mobility systems leads to a degradation in system performance. While these devices are relatively inexpensive and reliable, they suffer from several limitations. First, the sample volume through the detector is small, so to increase spectrometer sensitivity either the detector electronics must have extremely high sensitivity, requiring expensive electronics, or a concentrator is required, adding to system complexity. In addition, a gate and gating electronics are usually needed to control the injection of ions into the drift tube.

FAIM spectrometry was developed in the former Soviet Union in the 1980's. FAIM spectrometry allows a selected ion to pass through a filter while blocking the passage of undesirable ions. Conventional FAIM spectrometers are large and expensive, e.g., the entire device is nearly a cubic foot in size and costs over $25,000. These systems are not suitable for use in applications requiring small detectors. They are also relatively slow, taking as much as one minute to produce a complete spectrum of the sample gas, are difficult to manufacture and are not mass producible.

SUMMARY OF THE INVENTION

It is therefore an object of this invention to provide a FAIM filter and detection system which can more quickly and accurately control the flow of selected ions to produce a sample spectrum than conventional FAIM devices.

It is a further object of this invention to provide such a filter and detection system which can detect multiple preselected ions without having to sweep the bias voltage.

It is a further object of this invention to provide such a filter and detection system which can even detect selected ions without a bias voltage.

It is a further object of this invention to provide such a filter and detection system which can detect ions spatially based on the ions' trajectories.

It is a further object of this invention to provide such a filter and detection system which has a very high resolution.

It is a further object of this invention to provide such a filter and detection system which can detect selected ions faster than conventional detection devices.

It is a further object of this invention to provide such a filter and detection system which has a sensitivity of parts per billion to parts per trillion.

It is a further object of this invention to provide such a filter and detections system which may be packaged in a single chip.

It is further object of this invention to provide such filter and detection system which is cost effective to implement and produce.

The invention results from the realization that an extremely small, accurate and fast FAIM filter and detection system can be achieved by defining a flow path between a sample inlet and an outlet using a pair of spaced substrates and disposing an ion filter within the flow path, the filter including a pair of spaced electrodes, one electrode associated with each substrate and a controller for selectively applying a bias voltage and an asymmetric periodic voltage across the electrodes to control the path of ions through the filter.

The invention results from the further realization that by providing an array of filters, each filter associated with a different bias voltage, the filter may be used to detect multiple selected ions without sweeping the bias voltage.

The invention results from the realization that by varying the duty cycle of the periodic voltage, no bias voltage is required.

The invention results from the further realization that by segmenting the detector, ion detection may be achieved with greater accuracy and resolution by detecting ions spatially according to the ions' trajectories as the ions exit the filter.

This invention features a micromechanical field asymmetric ion mobility filter for a detection system. There is a pair of spaced substrates defining between them a flow path between a sample inlet and an outlet, an ion filter disposed in the path and including a pair of spaced filter electrodes, one electrode associated with each substrate and an electrical controller for applying a bias voltage and an asymmetric periodic voltage across the ion filter electrodes for controlling the paths of ions through the filter.

In a preferred embodiment there may be a detector, downstream from the ion filter, for detecting ions that exit the filter. The detector may include a plurality of segments, the segments separated along the flow path to spatially separate the ions according to their trajectories. There may be confining electrodes, responsive to the electrical controller, for concentrating selected ions as they pass through the filter. The confining electrodes may be silicon.

The silicon electrodes may act as spaces for spacing the substrates. There may be heater for heating the flow path. The heater may include the ion filter electrodes. The electrical controller may include means for selectively applying a current through the filter electrodes to heat the filter electrodes. The substrate may be glass. The glass may be Pyrex®. There may be an ionization source, upstream from the filter, for ionizing a fluid flow from the sample inlet. The ionization source may include a radioactive source. The ionization source may include an ultraviolet lamp. The ionization source may include a corona discharge device. There may be a clean air outlet for introducing purified air into the flow path. There may be a pump in communication with the flow path, for regulating a fluid flow through the flow path.

The invention also features a field asymmetric ion mobility filter and detection system. There is a housing having a flow path between a sample inlet and an outlet, an ion filter disposed in the flow path and including a pair of spaced filter electrodes, an electrical controller for applying a bias voltage and an asymmetric periodic voltage across the ion filter electrodes for controlling the path of ions through the filter, and a segmented detector, downstream from the ion filter, its segments separated along the flow path to spatially separate the ions according to their trajectories.

In a preferred embodiment there may be confining electrodes, responsive to the electrical controller, for concentrating the ions as they pass through the filter. The confining electrode may be silicon. The silicon electrodes may act as a spacer for spacing the filter electrodes. There may be a heater for heating the flow path. The heater may include the ion filter electrodes. The electrical controller may include means for selectively applying current through the filter electrodes to heat the filter electrodes. There may be an ionization source upstream from the filter for ionizing fluid flow from the sample inlet. The ionization source may include a radioactive source. The ionization source may include an ultraviolet lamp. The ionization source may include a corona discharge device. There may be a clean air inlet for introducing purified air into the flow path. There may be a pump in communication with the flow path for regulating a fluid flow through the flow path.

The invention also features a field asymmetric ion mobility filter array. There is a housing defining at least one flow path between a sample inlet and an outlet, a plurality of ion filters disposed within the housing, each ion filter including a pair spaced filter electrodes, and an electrical controller for applying a bias voltage and an asymmetric periodic voltage across each pair of ion filter electrodes for controller the path of ions through each filter.

In a preferred embodiment each ion filter may be associated with one of the flow paths. There may be a detector downstream from each ion filter for detecting ions that exit each said filter. Each detector may include a plurality of segments, the segments separated along the flow path to spatially separate the ions according to their trajectories. There may be a plurality of confining electrodes, responsive to the electrical controller, for concentrating the ions as they pass through each filter. Each confining electrode may be silicon. The silicon electrode may act as a spacer for spacing the filter electrodes. There may be a heater for heating the at least one flow path. The heater may include each pair of ion filter electrodes. The electrical controller may include means for selectively applying a current through each pair of filter electrodes to heat the filter electrodes. There may be an ionization source upstream from each filter for ionizing a fluid flow from the sample inlet. The ionization source may be a radioactive source. The ionization source may be an ultraviolet lamp. The ionization source may be a corona discharge device. There may be a clean air inlet for introducing purified air into at least one flow path. There may be a pump in communication with each flow path for regulating a fluid flow through each flow path.

The invention also features an uncompensated field asymmetric ion mobility filter for a detection system. There is a housing having a flow path between a sample inlet and an outlet, an ion filter disposed in the path and including a pair of spaced filter electrodes, an electrical controller for applying an uncompensated asymmetric periodic voltage across the ion filter for controlling the path of ions through the ion filter, and a selection circuit for selectively adjusting the duty cycle of the periodic voltage to target a selected specie or species of ion to be detected.

In a preferred embodiment there may be a detector downstream from the ion filter for detecting ions that exit the filter. The detector may include a plurality of segments, the segments separated along the flow path to spatially separate the ions according to their trajectories. There may be a confining electrode, responsive to the electrical controller, for concentrating the ions as they pass through the filter. The confining electrode may be silicon. The silicon electrode may act as a spacer for spacing the filter electrodes. There may be a heater for heating the flow path. The heater may include the ion filter electrodes. The electrical controller may include means for selectively applying a current through the filter electrodes to heat the filter electrodes. There may be an ionization source, upstream from the filter, for ionizing a fluid flow from sample inlet. The ionization source may include a radioactive source. The ionization source may include an ultraviolet lamp. The ionization source may include a corona discharge device. There may be a clean air inlet for introducing purified air into the flow path. There may be a pump in communication with the flow path for regulating a fluid flow through the flow path.

The invention also features a field asymmetric ion mobility filter. There is a housing having a flow path between a sample inlet and an outlet, an ion filter disposed in the flow path and including a pair of spaced filter electrodes, a pair of confining electrodes transverse to the flow path, and an electrical controller for applying a first bias voltage and an asymmetric periodic voltage across the ion filter electrodes and for applying a second bias voltage across the confining electrodes for controlling the path of ions through the filter.

In a preferred embodiment there may be a detector downstream from the ion filter for detecting ions that exit the filter. The detector may include a plurality of segments, the segments separated along the flow path to spatially separate the ions according to their trajectories. The confining electrodes may be silicon. The silicon electrodes may act as a spacer for spacing the filter electrodes. There may be a heater for heating the flow path. The heater may include the ion filter electrodes. The heater may include the confining electrodes. The electrical controller may include means for selectively applying a current through the filter electrodes to heat the filter electrodes. The electrical controller may include means for selectively applying a current through the confining electrodes to heat the confining electrodes. There may be an ionization source upstream from the filter for ionizing fluid flow from the sample inlet. The ionization source may include a radiation source. The ionization source may include an ultraviolet lamp. The ionization source may be a corona discharge device. There may be a clean air inlet for introducing purified air into the flow path. There may be a pump in communication with the flow path for regulating a fluid flow through the flow path.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Other objects, features and advantages will occur to those skilled in the art from the following description of a preferred embodiment and the accompanying drawings, in which.

DETAILED DESCRIPTION OF THE INVENTION

A description of preferred embodiments of the invention follows.

Figure 1:
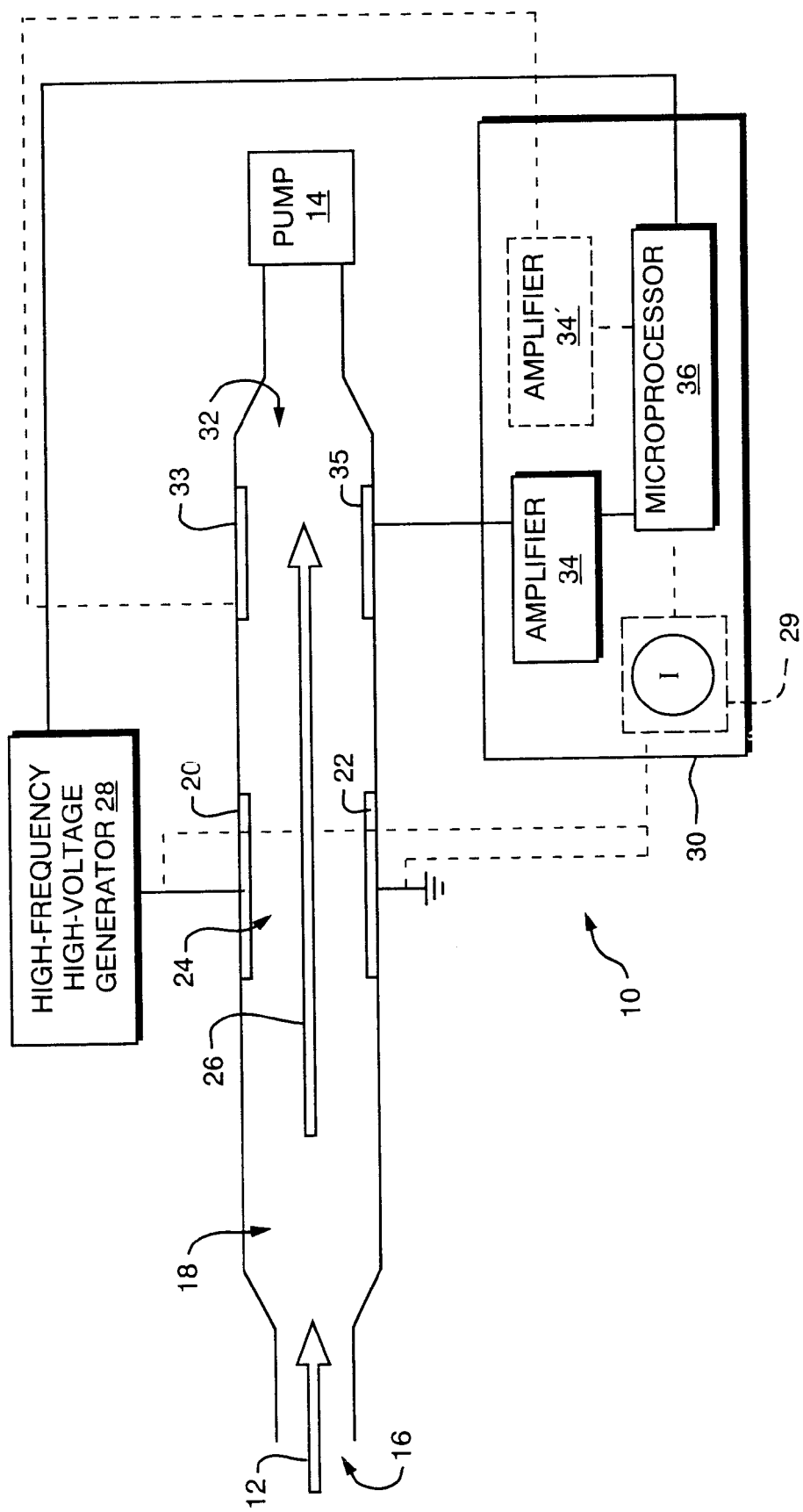
FIG. 1 is a schematic block diagram of the micromachined filter and detection system according to the present invention.

FAIM spectrometer 10, FIG. 1, operates by drawing a gas, indicated by arrow 12, via pump 14, through inlet 16 into ionization region 18. The ionized gas is passed between parallel electrode plates 20 and 22, which comprise ion filter 24, following flow path 26. As the gas ions pass between plates 20 and 22, they are exposed to an asymmetric oscillating electric field between electrode plates 20 and 22 induced by a voltage applied to the plates by voltage generator 28 in response to electronic controller 30

As ions pass through filter 24, some are neutralized by plates 20 and 22 while others pass through and are sensed by detector 32. Detector 32 includes a top electrode 33 at a predetermined voltage and a bottom electrode 35, typically at ground. Top electrode 33 deflects ions downward to electrode 35. However either electrode may detect ions depending on the ion and the voltage applied to the electrodes. Moreover, Multiple ions may be detected by using top electrode 33 as one detector and bottom electrode 35 as a second detector. Electronic controller 30 may include for example, amplifier 34 and microprocessor 36. Amplifier 34 amplifies the output of detector 32, which is a function of the charge collected by detector 34, and provides the output to microprocessor 36 for analysis. Similarly, amplifier 34', shown in phantom, may be provided where electrode 33 is also utilized as a detector.

Figure 2:
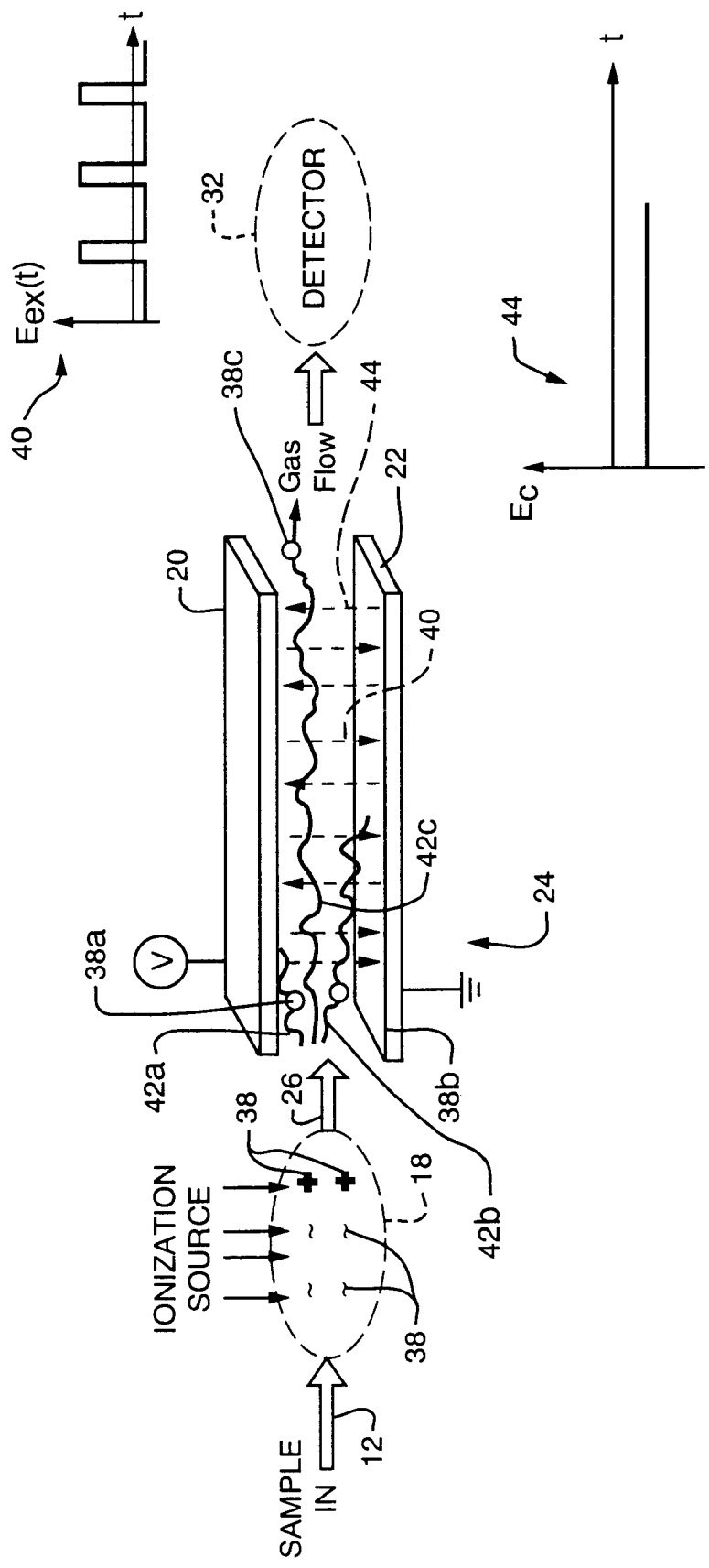
FIG. 2 is a schematic representation of the ions as they pass through the filter electrodes of FIG. 1 toward the detector.

As ions 38, FIG. 2, pass through alternating asymmetric electric field 40, which is transverse to gas flow 12, electric field 40, causes the ions to "wiggle" along paths 42a, 42b and 42c. Field 40 is typically in the range of ±(1000–2000) volts dc and has a maximum field strength of 40,000 V/cm. The path taken by a particular ion is a function of its mass, size, cross-section and charge. Once an ion reaches electrode 20 or 22, it is neutralized. A second, bias or compensation field 44, typically in the range of ±2000 V/cm or ±100 volts dc, is concurrently induced between electrodes 20 and 22 by as bias voltage applied to plates 20 and 22, also by voltage generator 28, FIG. 1, in response to microprocessor 36 to enable a preselected ion species to pass through filter 24 to detector 32. Compensation field 44 is a constant bias which offsets alternating asymmetric field 40 to allow the preselected ions, such as ion 38c to pass to detector 32. Thus, with the proper bias voltage, a particular species of ion will follow path 42c while undesirable ions will follow paths 42a and 42b to be neutralized as they encounter electrode plates 20 and 22.

The output of FAIM spectrometer 10 is a measure of the amount of charge on detector 32 for a given bias voltage 44. The longer filter 24 is set at a given compensation bias voltage, the more charge will accumulate on detector 32. However, by sweeping compensation voltage 44 over a predetermined voltage range, a complete spectrum for sample gas 23 can be achieved. The FAIM spectrometer according to the present invention requires typically less than thirty seconds and as little as one second to produce a complete spectrum for a given gas sample.

Figure 3A:
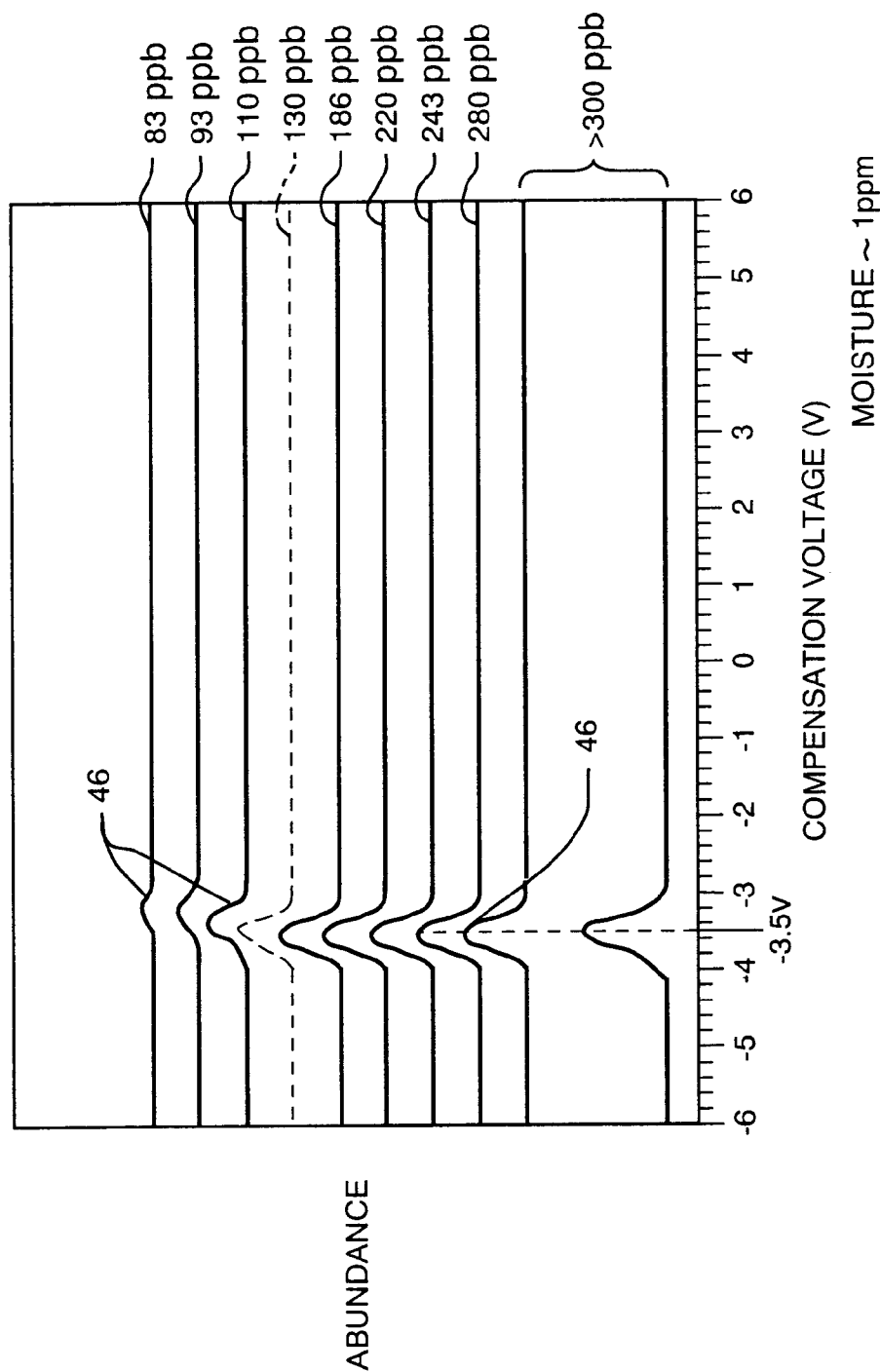
FIG. 3A is a graphical representation of the bias voltage required to detect acetone and the sensitivity obtainable.
Figure 3B:
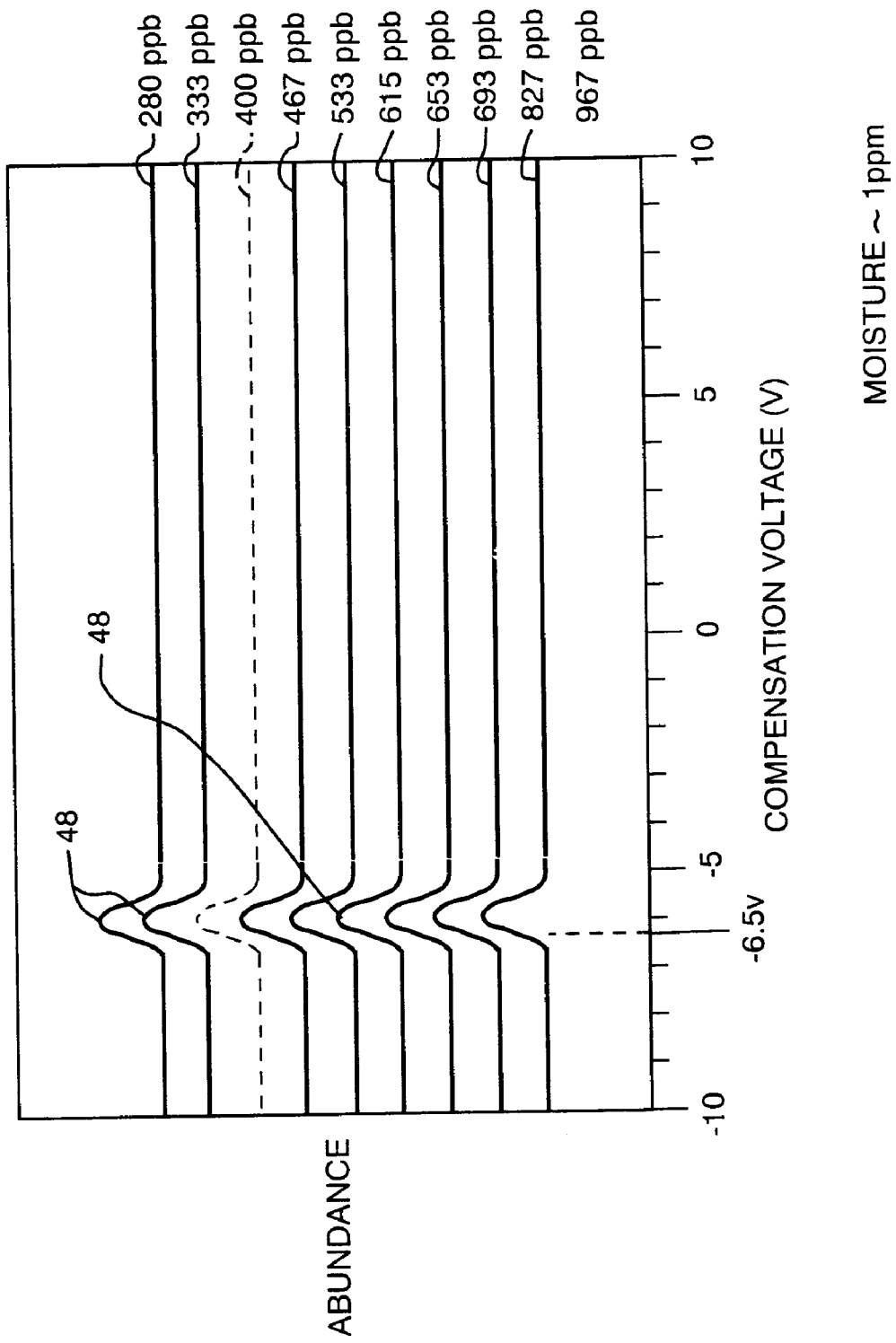
FIG. 3B is a representation, similar to FIG. 3A, of the bias voltage required to detect Diethyl methyl amine.

By varying compensation bias voltage 44 the species to be detected can be varied to provide a complete spectrum of the gas sample. For example, with a bias voltage of 3.5 volts acetone was detected as demonstrated by concentration peaks 46, FIG. 3A in concentrations as low as 83 parts per billion. In contrast, at a bias voltage of −6.5 volts, diethyl methyl amine, peaks 48, FIG. 3B, was detected in concentrations as low as 280 parts per billion.

Figure 4:
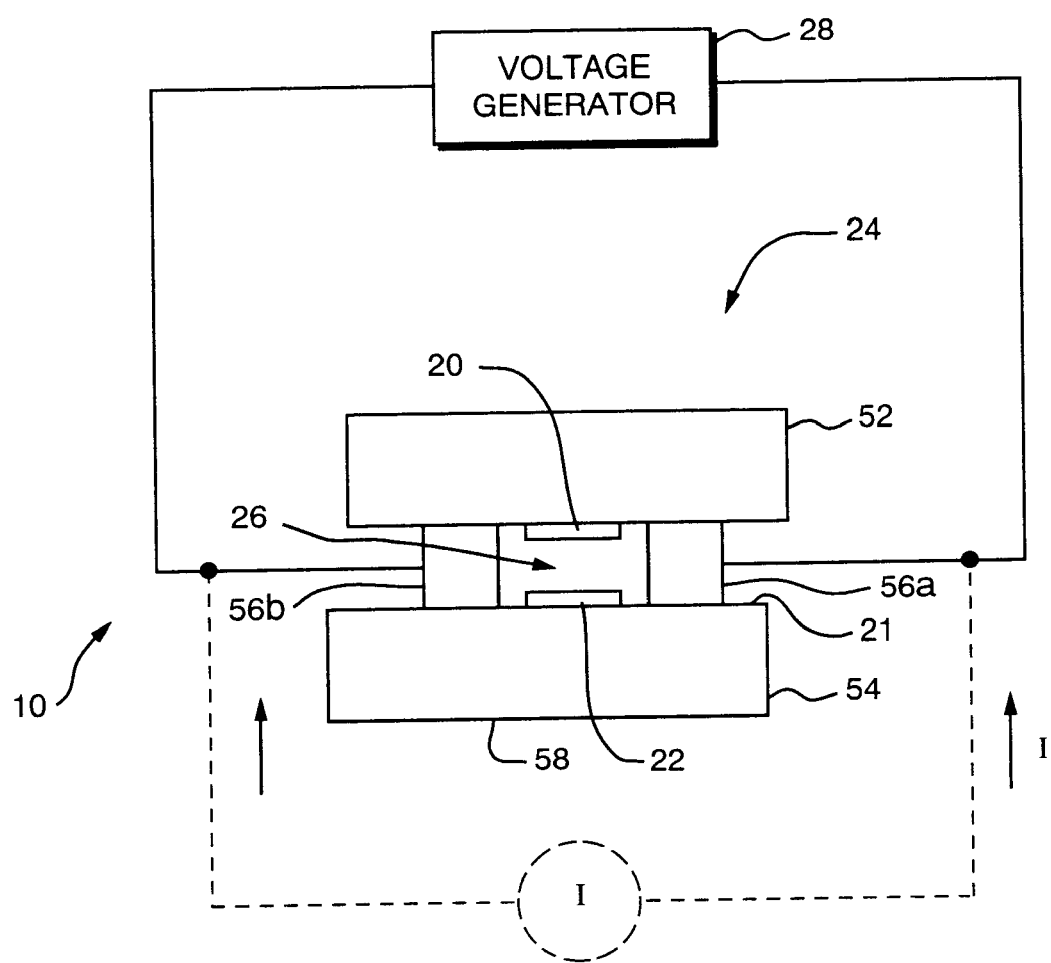
FIG. 4 is a cross sectional of the view of the spaced, micromachined filter according to the present invention.

Filter 24, FIG. 4, is on the order of one inch is size. Spectrometer 10 includes spaced substrates 52 and 54, for example glass such as Pyrex® available from Corning Glass, Corning, N.Y., and electrodes 20 and 22, which may be example gold, titanium, or platinum, mounted or formed on substrates 52 and 54, respectively. Substrates 52 and 54 are separated by spacers 56a and 56b which may be formed by etching or dicing silicon wafer. The thickness of spacers 56a and 56b defines the distance between electrodes 20 and 22. Moreover, applying the same voltage to silicon spacers 56a–b, typically ±(10–1000) volts dc) transforms spacers 56a–b into electrodes which produce a confining electric field 58, which guides or confines the ions' paths to the center of flow path 26. This increases the sensitivity of the system by preserving more ions so that more ions strike detector 34. However, this is not a necessary limitation of the invention.

To maintain accurate and reliable operation of spectrometer 10, neutralized ions which accumulate on electrode plates 20 and 22 must be purged. This may be accomplished by heating flow path 26. For example, controller 30, FIG. 1, may include current source 29, shown in phantom, which provides, in response to microprocessor 36, a current I to electrode plates 20 and 22 to heat the plates, removing accumulated molecules. Similarly, current I may instead be applied to spacer electrodes 56a and 56b, FIG. 4, to heat flow path 26 and clean plates 20 and 22.

Figure 5:
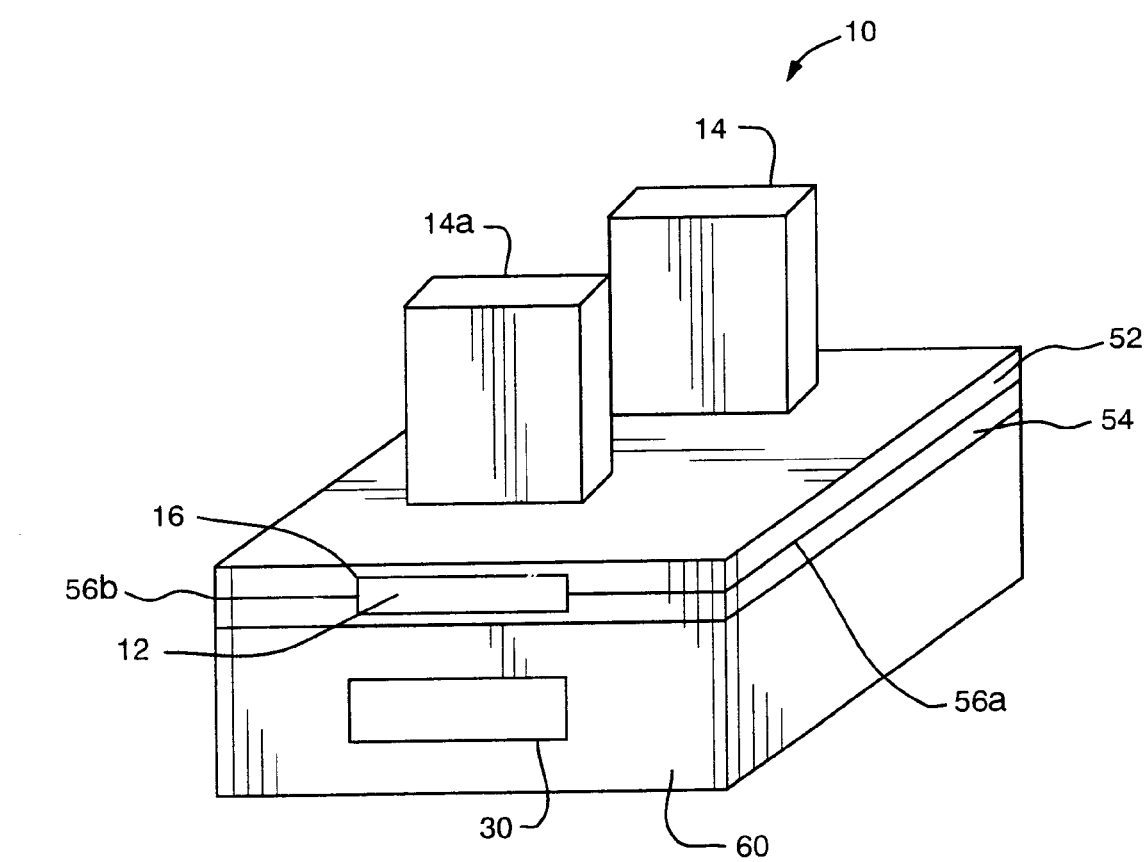
FIG. 5 is a three dimensional view of the packaged micromachined filter and detection system, including fluid flow pumps, demonstrating the miniaturized size which maybe realized.

Packaged FAIM spectrometer 10, FIG. 5, may be reduced in size to one inch by one inch by one inch. Pump 14 is mounted on substrate 52 for drawing a gas sample 12 into inlet 16. Clean dry air may be introduced into flow path 26, FIG. 1, by recirculation pump 14a prior to or after ionization of the gas sample. Electronic controller 30 may be etched into silicon control layer 60 which combines with substrates 52 and 54 to form a housing for spectrometer 10. Substrates 52 and 54 and control layer 60 may be bonded together, for example, using anodic bonding, to provide an extremely small FAIM spectrometer. Micro pumps 14 and 14a provide a high volume thoughput which further expedites the analysis of gas sample 12. Pumps 14 and 14a may be, for example, conventional miniature disk drive motors fitted with small centrifugal air compressor rotors or micromachined pumps, which produce flow rates of 1 to 4 liters per minute. One example of pump 14 is available from Sensidyne, Inc., Clearwater, Fla.

Figure 6:
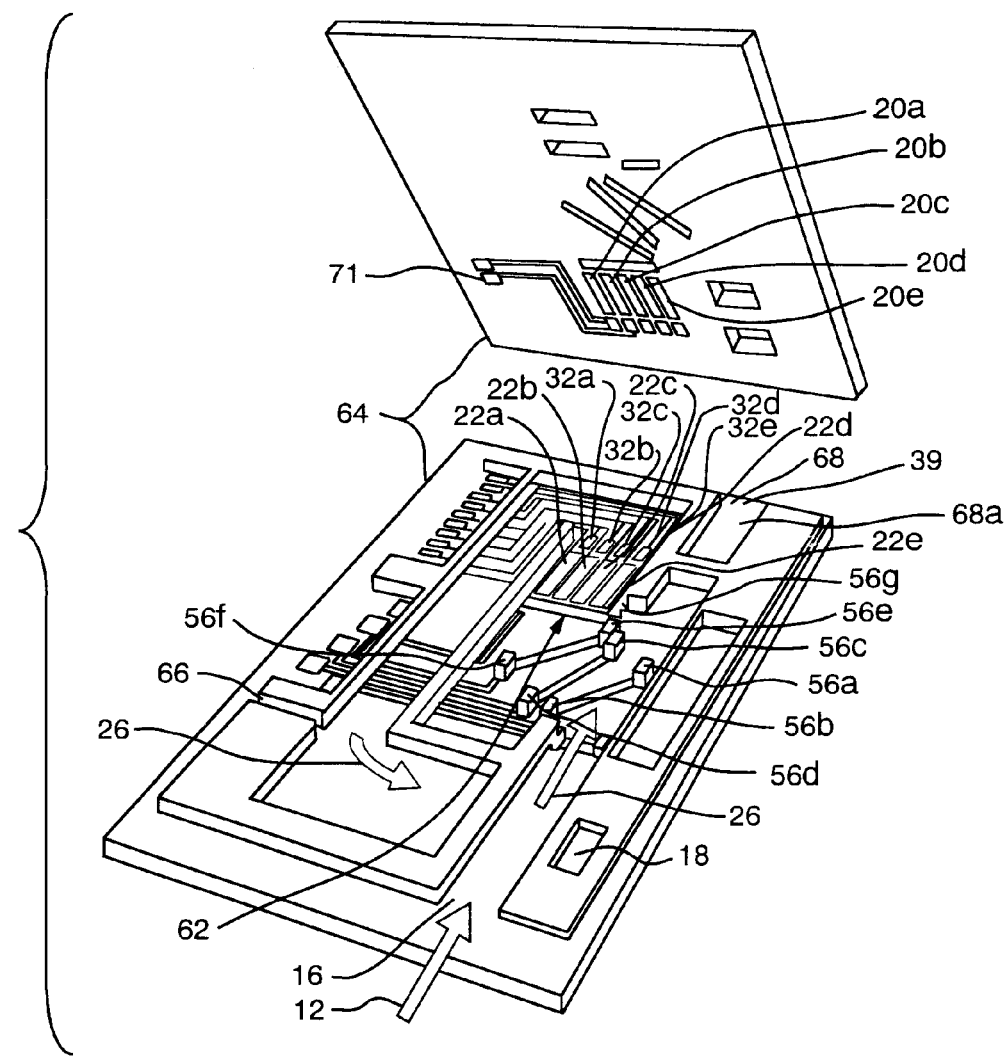
FIG. 6 is an exploded view of one embodiment according to the present invention in which an array of filters and detectors are disposed in a single flow path.

While the FAIM spectrometer according to the present invention quickly produces a spectrum for a particular gas sample, the time for doing so may be further reduced with an array of filters 32. FAIM spectrometer 10, FIG. 6, may include filter array 62, a single inlet 16 and single flow path 26. Sample gas 23 is guided by confining electrodes 56a–h to filter array 62 after passing by ionization source 18, which may include an ultraviolet light source, a radioactive device or corona discharge device. Filter array 62 includes, for example, paired filter electrodes 20a–d and 22a–e and may simultaneously detect different ion species by applying a different compensation bias voltage 44, FIG. 2, to each electrode pair and sweeping each electrode pair over a different voltage range greatly reducing the sweep time. However, array 62 may include any number of filters depending on the size of the spectrometer. Detector array 64, which includes detectors 32a–e, detects multiple selected ion species simultaneously, thereby reduce the time necessary to obtain a spectrum of the gas sample 12. The electrode pairs share the same asymmetric periodic ac voltage 40.

Clean dry air may be introduced into flow path 26 through clean air inlet 66 via recirculator pump 14a, FIG. 5. Drawing in clean dry air assists in reducing the FAIM spectrometer's sensitivity to humidity. Moreover, if the spectrometer is operated without clean dry air and a known gas sample is introduced in the device, the device can be used as a humidity sensor since the resulting spectrum will change with moisture concentration from the standardized spectrum for the given sample.

Figure 7:
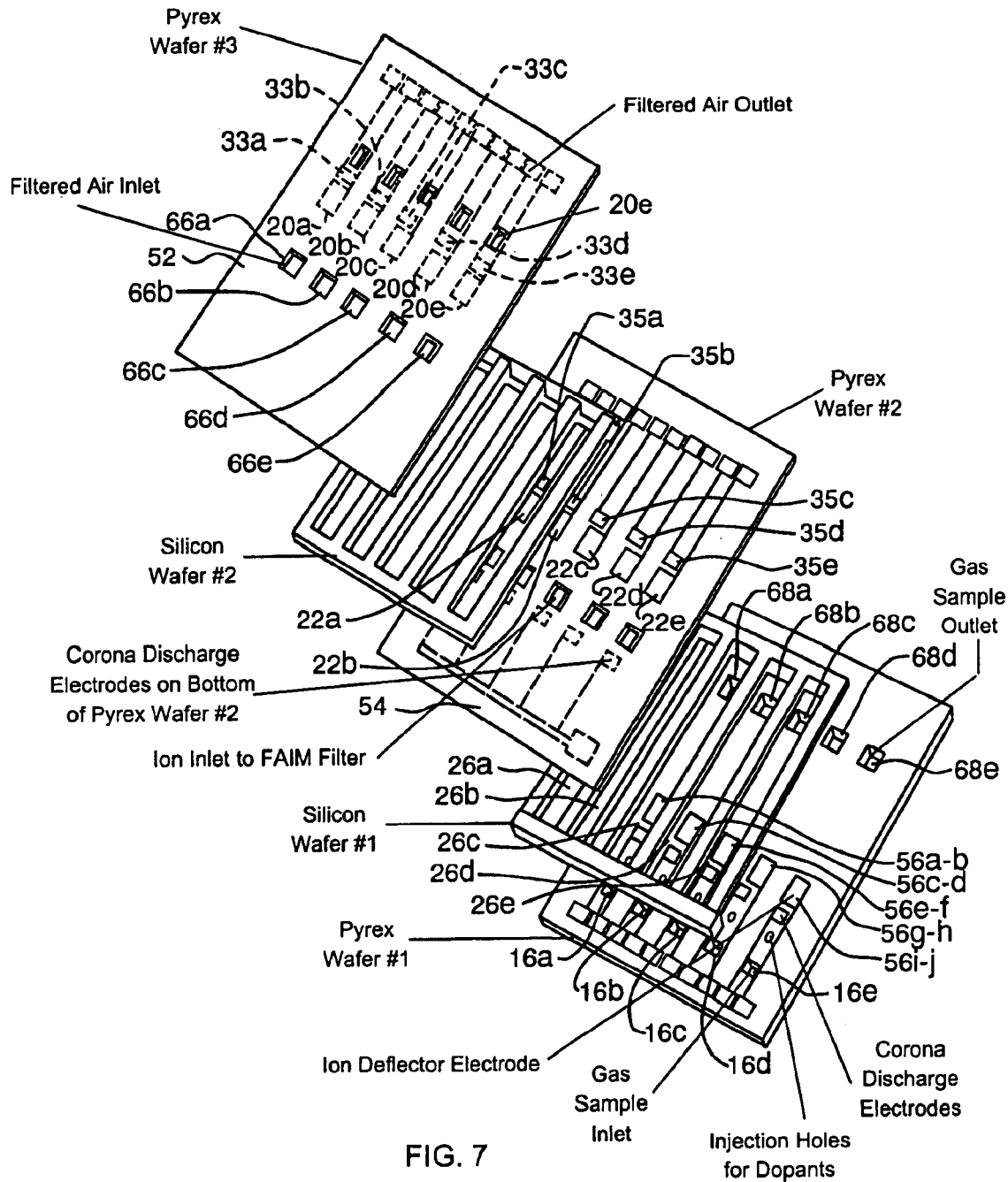
FIG. 7 is an exploded view, similar to FIG. 6, in which the array of filters is stacked and one filter and detector is associated with a single flow path.

However, rather than each filter 32a–e of filter array 62 sharing the same flow path 26, individual flow paths 26a–e, FIG. 7, may be provided so that each flow path has associated with it, for example, inlet 16a, ionization region 18a, confining electrodes 56a', 56b', ion filter electrode pair 20a, 22a, detector electrode pair 33a, 35a, and exit port 68a.

Figure 8:
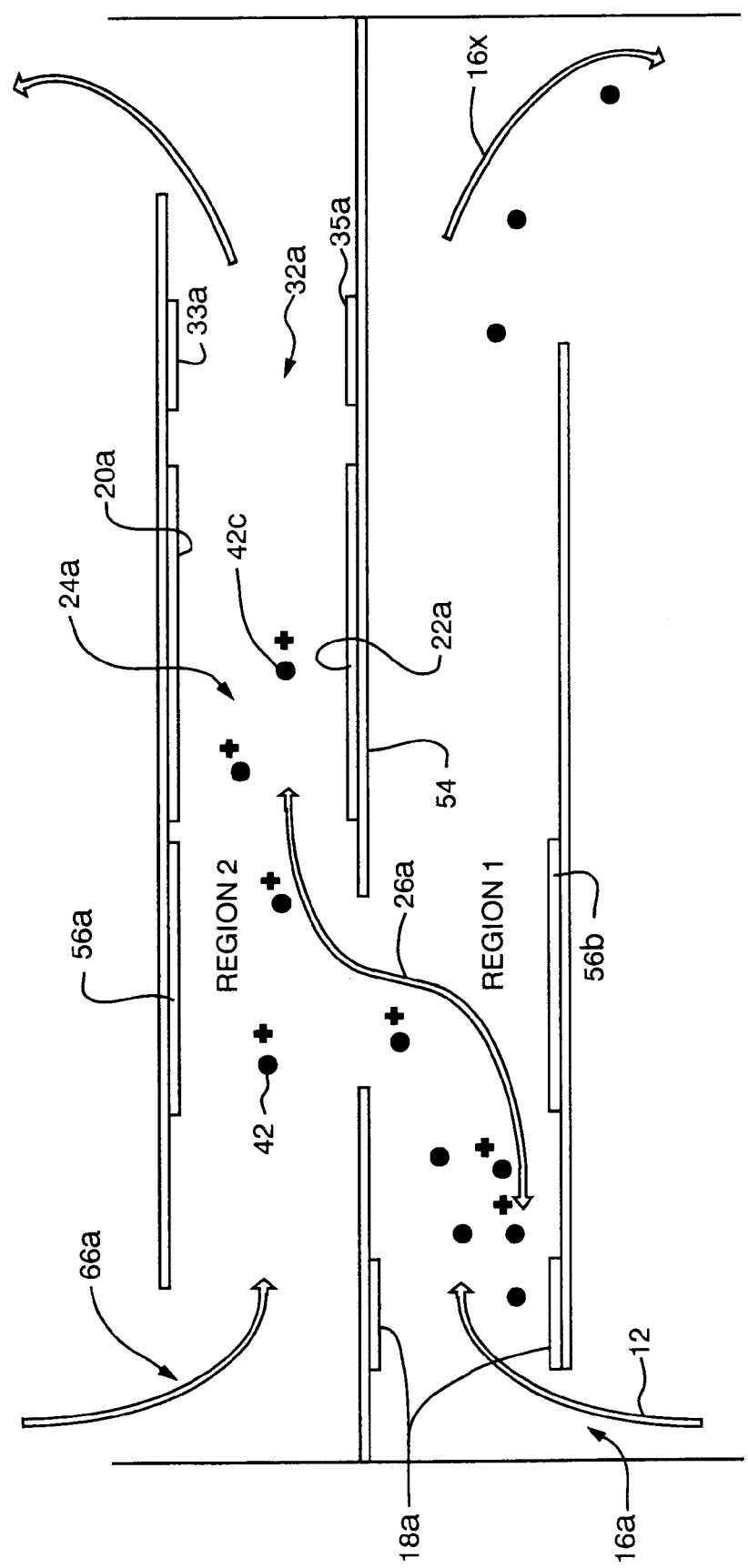
FIG. 8 is a cross sectional representation of a single flow path of the arrayed filter and detector system of FIG. 7.

In operation, sample gas 12 enters sample inlet 16a, FIG. 8, and is ionized by, for example, a corona discharge device 18a. The ionized sample is guided towards ion filter 24a by confining electrodes 56a. As ions pass between ion filter electrodes 20a and 22a, undesirable ions will be neutralized while selected ions will pass through filter 24a to be detected by detector 32a.

Figure 9:
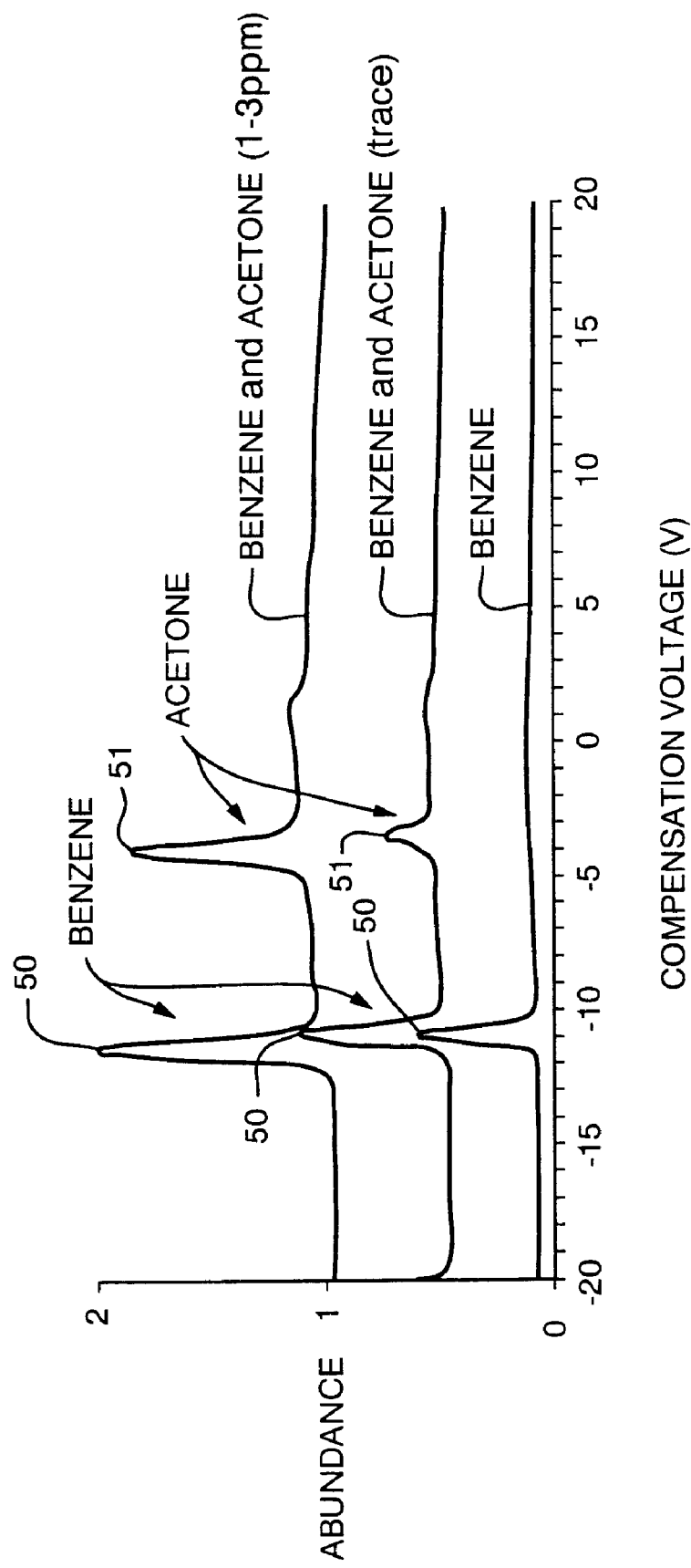
FIG. 9 is a graphical representation demonstrating simultaneous multiple detections of benzene and acetone.

As shown in FIG. 9, multiple, simultaneous detections were made of Benzene, peaks 50 and acetone peaks 51, demonstrating the advantage of the arrayed filters and detectors according to the present invention.

Figure 10:
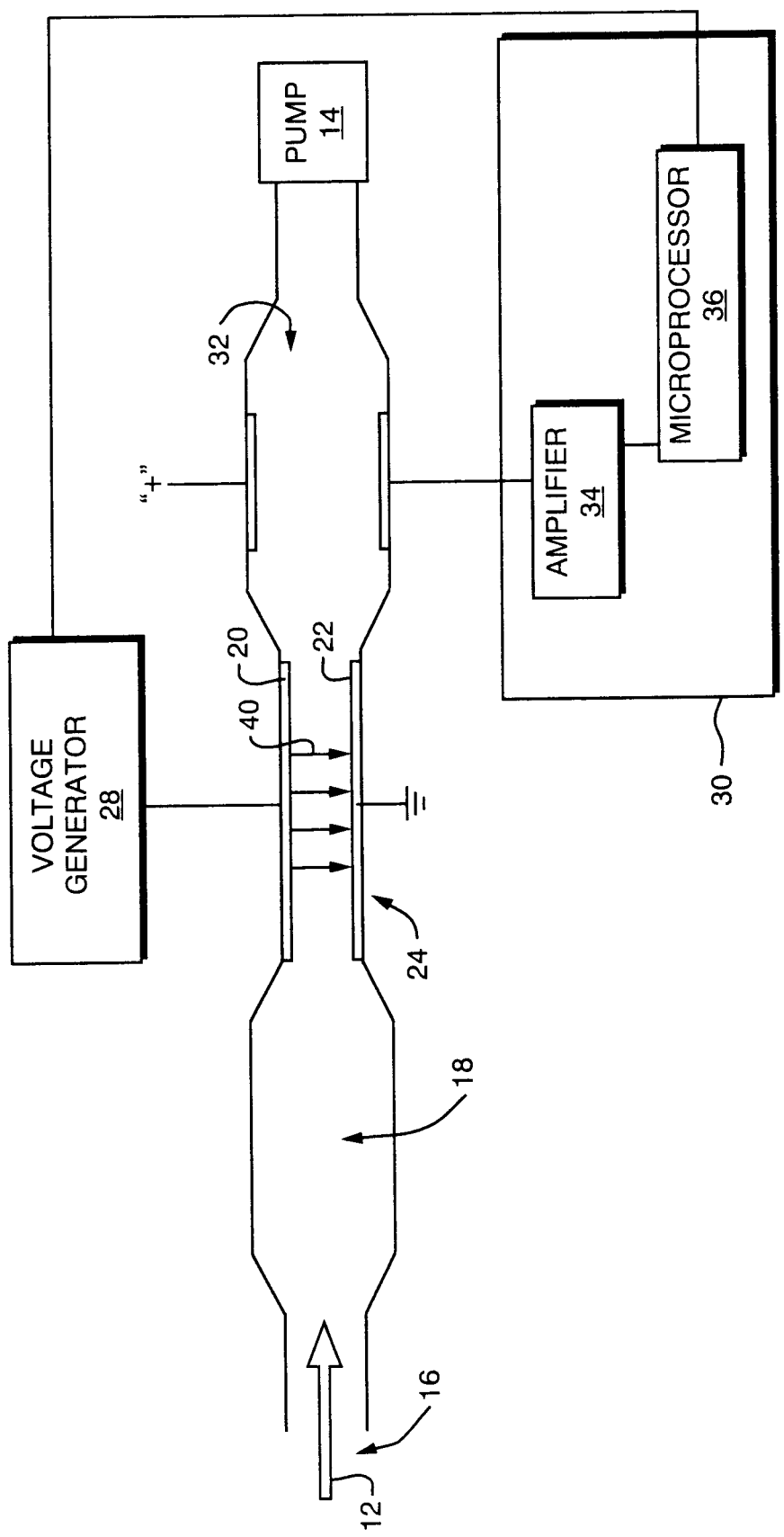
FIG. 10 is a schematic block diagram, similar FIG. 1, in which the filter is not compensated by a bias voltage and the duty cycle of the periodic voltage is instead varied to control the flow of ions through the filter.
Figure 11:
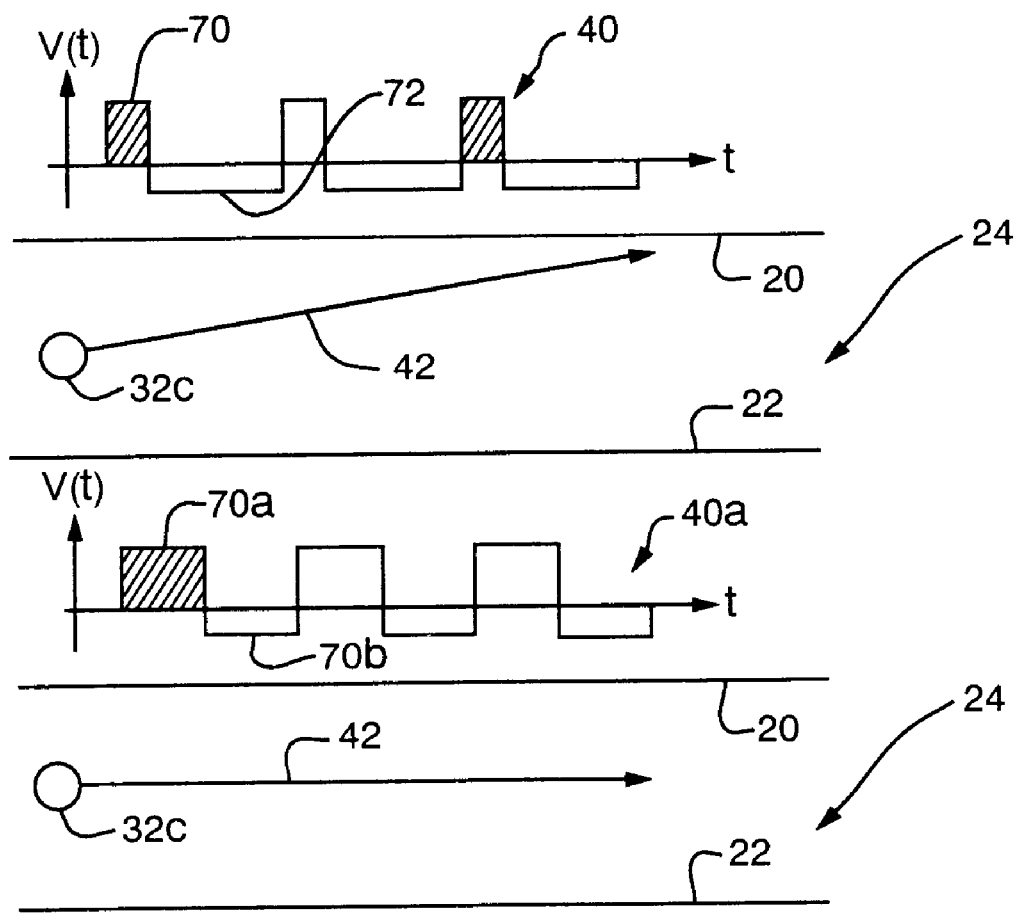
FIG. 11 is a graphical representation of an asymmetric periodic voltage having a varying duty cycle which is applied to the filter of FIG. 9 to filter selected ions without a bias voltage.

It has also been found that a compensation bias voltage is not necessary to detect a selected specie or species of ion. By varying the duty cycle of the asymmetric periodic voltage applied to electrodes 20 and 22 of filter 24, FIG. 10, there is no need to apply a constant bias voltage to plate electrodes 20 and 22. Voltage generator 28, in response to control electronics 30 varies the duty cycle of asymmetric alternating voltage 40. By varying the duty cycle of periodic voltage 40, FIG. 11, the path of selected ion 32c may be controlled. As an example, rather than a limitation, the duty cycle of field 40 may be one quarter: 25% high, peak 70, and 75% low, valley 72, and ion 38c approaches plate 20 to be neutralized. However, by varying the duty cycle of voltage 40a to 40%, peak 70a, ion 38c passes through plates 20 and 22 without being neutralized. Typically the duty cycle is variable from 10–50% high and 90–50% low. Accordingly, by varying the duty cycle of field 40, an ion's path may be controlled without the need of a bias voltage.

Figure 12:
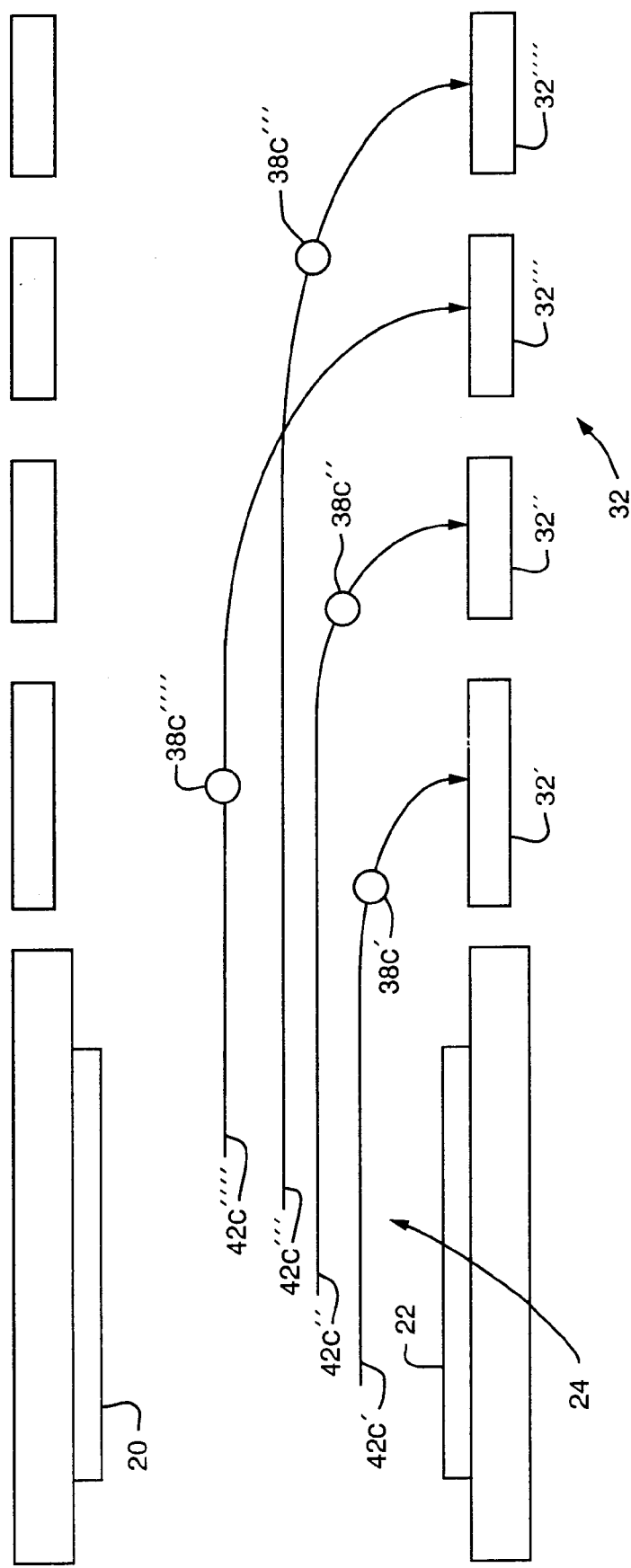
FIG. 12 is a schematic diagram of a filter and detector system in which the detector is segmented to spatially detect ions as they exit the filter.

To improve FAIM spectrometry resolution even further, detector 32, FIG. 12, may be segmented. Thus as ions pass through filter 24 between filter electrodes 20 and 22, the individual ions 38c"–38c"" may be detected spatially, the ions having their trajectories 42'–42'" determined according to their size, charge and cross section. Thus detector segment 32' will have one a concentration of one species of ion while detector segment 32" will have a different ion species concentration, increasing the spectrum resolution as each segment may detect a particular ion species.

Although specific features of the invention are shown in some drawings and not in others, this is for convenience only as each feature may be combined with any or all of the other features in accordance with the invention.

Other embodiments will occur to those skilled in the art and are within the following claims:

While this invention has been particularly shown and described with references to preferred embodiments thereof, it will be understood by those skilled in the art that various changes in form and details may be made therein without departing from the scope of the invention encompassed by the appended claims.

What is claimed is:

1. Apparatus for measurement of a component of a gas sample, comprising:

a flow path extending between a sample inlet and an outlet, said sample including a chemical compound, an ion filter disposed in the flow path, the ion filter comprising electrodes separated by an analytical gap, an electrical input configured to apply an asymmetric periodic voltage to said filter for forming an asymmetric field in said gap, said field for transversely dispersing ions in a sample in said ion filter, a controller input for selectively adjusting the condition of said field to enable ions representative of a compound in said sample to be separated from said dispersed ions according to their mobility in said field and according to said field condition, said filter issuing an ion output including said separated ions, a detector for generation of spectra information based on said ion output, said spectra having detected peaks representing detected ions in said ion output, at least one of said peaks being associated with said separated ions, a humidity sensor means for generating moisture-driven changes in said spectra, and said detector correlating said changes with said generated spectra and with said detected peaks for measurement of a component of said sample.

2. Apparatus of claim 1 wherein said component is the moisture content of said sample.

3. Apparatus of claim 1 wherein said component is a chemical compound.

4. Apparatus of claim 1 wherein said asymmetric field is a compensated RF field.

5. A field asymmetric ion mobility filter system for identification of compounds in a sample, comprising:

a flow path extending between a sample inlet and an outlet, said sample including a chemical compound, an ion filter disposed in the flow path, the ion filter comprising electrodes separated by an analytical gap, an electrical input configured to apply an asymmetric periodic voltage to said filter for forming an asymmetric field in said gap, said field for transversely dispersing ions in said ion filter, a controller input for selectively adjusting the condition of said field to enable ions representative of said compound to be separated from said dispersed ions according to their mobility in said field and according to said field conditions, said filter issuing an ion output including said separated ions, a detector for generation of spectra information based on said ion output, said spectra having detection peaks representing detected ions in said ion output, at least one of said peaks being associated with said separated ions, a humidity sensor for generating moisture-driven changes in said spectra for a given sample, said detector correlating said spectra and peak data for identification of said compound.

6. A field asymmetric ion mobility filter system comprising:

a flow path extending between a sample inlet and an outlet, an ion filter comprising electrodes opposite each other and separated by an analytical gap in said flow path, an electrical input configured to apply a signal with a dispersing asymmetric waveform to said filter electrodes for forming a displacement field in said gap for transversely dispersing ions in said filter, and a selection input configured for selectively adjusting a characteristic of said waveform to enable ion species to be separated according to their mobility in said displacement field with selected species being passed through said filter for detection and identification based on known effects of said waveform adjustment.

7. System of claim 6 wherein said signal operates without a DC bias.

8. System of claim 6 wherein the adjusted characteristic of said asymmetric waveform is its duty cycle.

9. A field asymmetric ion mobility system, comprising:

a support structure, inner surfaces of said support structure forming an enclosed flow path, said flow path extending along a longitudinal axis between a sample inlet and an outlet and accommodating a flow of ions, a plurality of electrodes associated with said support structure, an assigned set of said plurality of electrodes for confining the travel of ions in said flow of ions for focusing said confined ions in said flow path, at least two of said plurality of electrodes being insulated from each other and spaced apart by said support structure, said spaced electrodes generating an asymmetric displacement field in said flow path, said displacement field imparting transverse motion to ions in said flow of ions based on mobility of said ions in said displacement field, said displacement field being compensated, said compensation causing a species of said ions in said flow of ions to separate from said transversely moving ions, said species traveling toward said outlet and the remaining said transversely moving ions tending to contact said spaced electrodes and be neutralized, and said confining electrodes and said spaced electrodes cooperating for controlling the position of said selected ions traveling along said flow path, said selected ions flowing to said outlet for detection.

10. System of claim 9 wherein said plurality of electrodes includes a pair of filter electrodes and a pair of confining electrodes.

11. A field asymmetric ion mobility filter system comprising a housing structurally defining at least one enclosed flow channel for the flow of ions between a sample inlet and an outlet, a plurality of electrodes, an electronic drive source, an ion filter disposed in said at least one flow channel, said plurality of electrodes including a pair of spaced filter electrodes having inner surfaces oriented to face toward each other and forming an analytical gap therebetween, said electrode spacing fixed by said walls of said at least one flow channel, said drive source generating an asymmetric filter field between said filter electrodes, wherein said filter field is driven by said source to select a species of ions from said flow of ions in said gap to pass to said output, said drive source generating a compensated asymmetric control field between at least a pair of said electrodes for steering ions in said flow of ions toward a desired path of said flow channel between said filter electrodes, and wherein said selected ion species predominantly flows in said desired path toward said outlet as dictated by said electrodes.

12. System of claim 11 wherein said electrodes generate a field condition for separating said ions and are driven by an asymmetric RF signal applied by said source for generating an RF field condition that is compensated to return ones of said ions toward said path.

13. System of claim 11 wherein said signal applied to said electrodes for separating is compensated with a DC offset to return ones of said ions toward said path.

14. System of claim 11 wherein said signal applied to said electrodes for separating is compensated by adjusting waveform characteristics of the applied asymmetric signal to return ones of said ions toward said center of said flow channel.

15. System of claim 11 wherein said electrodes for transversely moving said ions toward said center of said flow channel are driven by a compensation signal applied by said source to enable said compensation of said RF field.

16. System of claim 11 wherein at least two of said electrodes are separated by a spacer arrangement.

17. System of claim 16 wherein said spacer arrangement is defined by said at least two electrodes generating a field condition for transversely moving ones of said ions toward the center of said flow channel.

18. System of claim 11 wherein at least two of said electrodes are separated by a spacer arrangement and wherein these said electrodes and said spacer arrangement form a closed vessel defining the flow channel open at its ends, said ions flowing in said vessel.

19. A field asymmetric ion mobility detection system comprising:
- an input part and an output part,
- at least a pair of substrates defining between them a flow path for the flow of ions from the input part to the output part,
- a plurality of the electrodes opposite each other in the flow path and defining at least one filter electrode associated with each substrate to form an ion filter section,
- an electronics part for controlling to the electrodes, and the electronics part applying an asymmetric periodic signal across the filter electrodes for generating a filter field for transversely directing the flow of ions to impact the electrodes, the field being compensated to pass a selected species of the ions in the flow of ions through the filter without impacting the filter electrodes according to differences in mobility of the ions in the compensated field, and
- the plurality of the electrodes also defining an array of spatially deployed detector electrodes associated with the substrates to form an ion detector, wherein the ions of the passed species deposit their charges on the detector electrodes, the detector electrodes collecting charges of a passed ion species according to the trajectory of the passed species, the species being identified based on charge collection and location of the electrodes for a given set of field conditions.

20. The system of claim 19 wherein the substrates are planar and have at least insulated surfaces along the flow path between the filter electrodes and the output part.

21. The system of claim 19 further comprising a plurality of dedicated flow paths communicating between the input part and the output part, wherein the arrangement of electrodes comprises an array of filter electrode pairs associated with the dedicated flow paths.

22. The system of claim 19 wherein the array of electrodes defines a segmented detector.

23. A field asymmetric ion mobility detection system comprising:
- spaced substrates defining between them an enclosed flow path, the flow path extending from an input part to an output part,
- a plurality of electrodes opposite each other and defined in the flow path, the plurality defining at least one filter electrode associated with each substrate to form an ion filter,
- an electronics part associated with the electrodes and configured to apply controlling signals to the filter electrodes, including applying an asymmetric periodic signal to said filter for changing the flow of ions in the flow path, and
- the substrates having a plurality of substrate surfaces forming a plurality of dedicated flow paths communicating with the output part, wherein the plurality of electrodes comprises an array of electrode pairs associated with the dedicated flow paths.

24. The system of claim 23 wherein the array of electrode pairs defines an array of filter electrode pairs associated with the dedicated flow paths.

25. The system of claim 23 wherein the array of electrodes defines an array of detector electrodes in the output part associated with the dedicated flow paths.

26. A field asymmetric ion mobility system comprising:
- an insulated structure having surfaces defining at least one enclosed flow path extending between a system input and a system output, said system input for the delivery of at least a portion of a sample flow to said flow path,
- a plurality of filter electrodes supported by said structure and associated with said at least one flow path, pairs of said electrodes having interior surfaces that face toward each other separated by a fixed analytical gap, forming a plurality of ion filters associated with said at least one flow path,
- said at least one flow path having a filter input for receipt of at least a part of said sample flow, said at least one ion filter presenting a filter field in said fixed gap, said field having asymmetrically alternating field conditions,
- means for supply of ions to said at least one filter,
- said filter field being compensated and filtering said ions in said gap by species, said filtering being based on differences in ion mobility in said field conditions, said at least one filter passing selected ions for detection according to said compensation, and
- said system output enabling identifying said passed selected ions according to said field conditions.

27. A field asymmetric ion mobility system comprising:
- a housing structure defining a plurality of enclosed flow paths extending between a sample input part and an output part, said input part supplying a flow of ions to said flow paths,
- pairs of opposed ion filter electrodes associated with said structure, said electrodes including plate electrodes and forming a plurality of independent ion filters associated with said flow paths,
- said structure including a support for enclosure of said flow paths and for the carrying of said electrodes separated by a gap, and
- at least one said filter for presenting a filter field in said gap with high and low field conditions, said filter field being compensated and filtering said ions in said gap according to ion mobility differences in said field conditions and passing selected ions for downstream detection according to said compensation.

* * * * *